/ / / / / / / / / / / / / / / / / / / / / / / / / / / / / / / / US011484388B2

(12) United States Patent
Levine

(10) Patent No.: US 11,484,388 B2
(45) Date of Patent: Nov. 1, 2022

(54) MOBILE ORTHODONTIC TREATMENT SYSTEM AND METHOD

(71) Applicant: AlignGo, LLC, Lexington, MA (US)

(72) Inventor: Sam William Levine, Harvard, MA (US)

(73) Assignee: AlignGo, LLC, Lexington, MA (US)

( * ) Notice: Subject to any disclaimer, the term of this patent is extended or adjusted under 35 U.S.C. 154(b) by 0 days.

(21) Appl. No.: 17/170,983

(22) Filed: Feb. 9, 2021

(65) Prior Publication Data

US 2021/0177545 A1 Jun. 17, 2021

Related U.S. Application Data

(63) Continuation of application No. 16/353,741, filed on Mar. 14, 2019, now Pat. No. 10,945,810.

(51) Int. Cl.
*A61C 7/00* (2006.01)
*A61B 6/14* (2006.01)
*A61C 9/00* (2006.01)
*A61B 6/00* (2006.01)
*A61G 3/06* (2006.01)
*A61B 5/00* (2006.01)
*A61C 19/00* (2006.01)
*B60P 3/025* (2006.01)
*B62D 63/06* (2006.01)

(52) U.S. Cl.
CPC ............... *A61C 7/00* (2013.01); *A61B 5/742* (2013.01); *A61B 6/14* (2013.01); *A61B 6/4417* (2013.01); *A61B 6/462* (2013.01); *A61C 7/002* (2013.01); *A61C 9/0053* (2013.01); *A61C 19/002* (2013.01); *A61G 3/062* (2013.01); *B60P 3/025* (2013.01); *B62D 63/06* (2013.01)

(58) Field of Classification Search
CPC ......... A61C 7/00; A61C 7/002; A61C 9/0053; A61C 19/002; A61B 5/742; A61B 6/14; A61B 6/4417; A61B 6/462; A61G 3/062; B60P 3/025; B62D 63/06
USPC ....................................................... 296/24.38
See application file for complete search history.

(56) References Cited

U.S. PATENT DOCUMENTS

| 2002/0028418 | A1 | 3/2002 | Farag et al. |
| 2003/0235265 | A1 | 12/2003 | Clinthorne et al. |
| 2005/0179878 | A1* | 8/2005 | Ohtsuka ................. A61B 6/447 355/30 |
| 2007/0102946 | A1 | 5/2007 | Blackwell et al. |
| 2008/0129068 | A1 | 6/2008 | Brummel et al. |

(Continued)

*Primary Examiner* — Joseph D. Pape
(74) *Attorney, Agent, or Firm* — Lando & Anastasi, LLP

(57) ABSTRACT

A mobile orthodontic treatment system includes comprising a mobile trailer and a panoramic machine provided within the trailer. The panoramic machine is configured to obtain a 2-D image of a patient's mouth and includes a base secured to the floor of the housing and a stanchion secured to the trailer by a bracket. The mobile orthodontic treatment system further includes a digital scanner and a monitor provided within the housing. The digital scanner is configured to obtain a 3-D image of the patient's mouth and display the image on the monitor. The digital scanner and the monitor are mounted on a wall of the housing by a wall mount articulating bracket. The mobile orthodontic treatment system further includes a lift assembly provided on one of a side and an end of the housing to enable disabled people to enter and exit the housing.

17 Claims, 15 Drawing Sheets

(56) References Cited

U.S. PATENT DOCUMENTS

| | | |
|---|---|---|
| 2010/0068676 A1 | 3/2010 | Mason et al. |
| 2013/0035955 A1 | 2/2013 | Torres |
| 2014/0035320 A1* | 2/2014 | Aguirre ................ B60P 7/0807 296/183.1 |
| 2017/0027532 A1* | 2/2017 | Joshi ........................ A61B 6/44 |

* cited by examiner

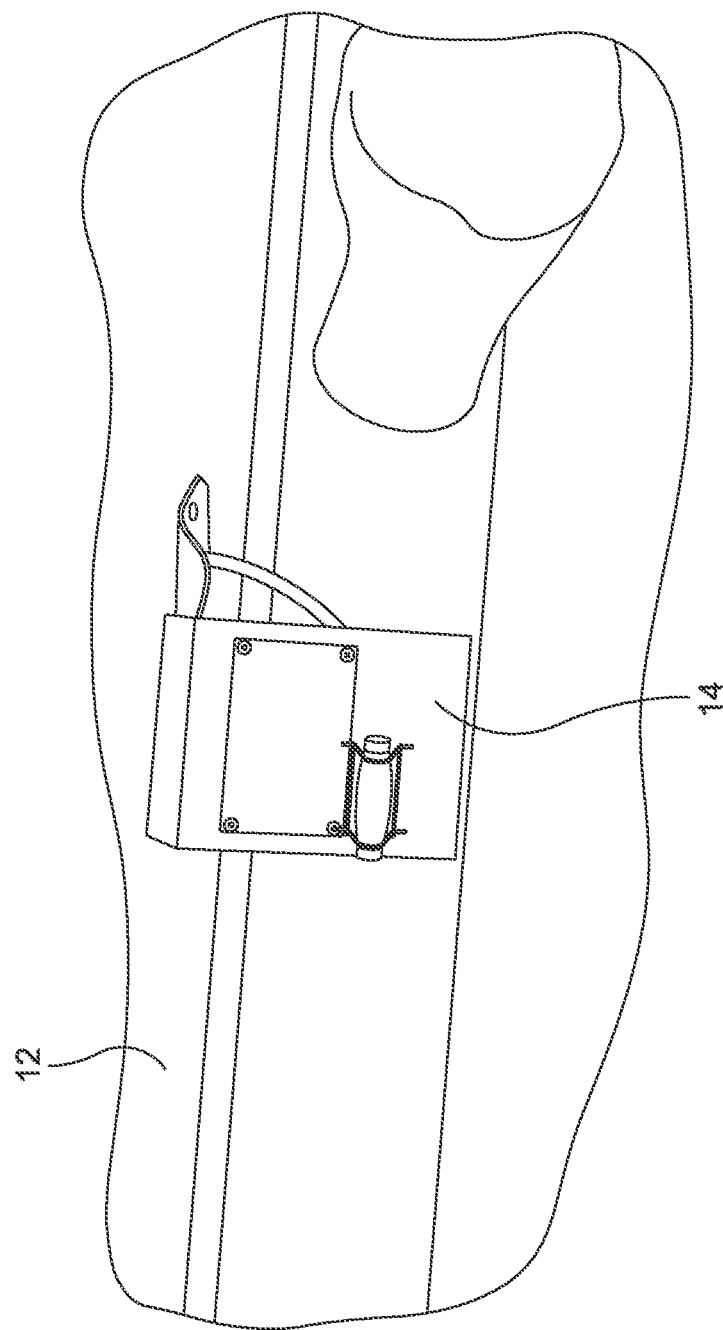

MOBILE ORTHODONTIC TREATMENT SYSTEM AND METHOD

RELATED APPLICATIONS

This application is a continuation of U.S. patent application Ser. No. 16/353,741, filed Mar. 14, 2019 titled "MOBILE ORTHODONTIC TREATMENT SYSTEM AND METHOD," which is hereby incorporated by reference in its entirety for all purposes.

FIELD OF THE DISCLOSURE

The present disclosure is generally related to orthodontic treatment facilities, and more particularly to a mobile orthodontic treatment system and method.

BACKGROUND OF THE DISCLOSURE

Orthodontic services are traditionally performed within a dental or orthodontic facility. Large equipment, such as dental panoramic radiography equipment, otherwise known as panoramic machines, require relatively large spaces to operate. A panoramic machine is a two-dimensional (2-D) dental X-ray examination that captures the entire mouth in a single image, including the teeth, upper and lower jaws, surrounding structures and tissues. Other equipment, such as digital scanners, are also required in the orthodontic facility.

Orthodontic services require a patient to visit the orthodontic facility for periodic treatment. Patients often take time from work or school to visit the orthodontic facility. There is a need for a mobile orthodontic treatment facility that can transported to the patient. For example, rather than the patient visiting the facility, the mobile system can be brought to the patient, whether it be a school or a place of work.

SUMMARY OF THE DISCLOSURE

The present disclosure is directed to a mobile orthodontic treatment system comprising a mobile trailer including a chassis and a housing supported by the chassis. The housing includes two sides, two opposite ends, a roof, and a floor, the chassis including a wheel assembly. The mobile orthodontic treatment system further includes a panoramic machine provided within the housing. The panoramic machine is configured to obtain a 2-D image of a patient's mouth and includes a base, an upright stanchion extending upwardly from the base, and an image detector. The base of the panoramic machine is secured to the floor of the housing, with the upright stanchion being secured to a side or an end of the housing by a bracket. The mobile orthodontic treatment system further includes a digital scanner and a monitor provided within the housing. The digital scanner is configured to obtain a 3-D image of the patient's mouth and display the image on the monitor. The digital scanner and the monitor are mounted on a wall of the housing by a wall mount articulating bracket configured to support the digital scanner and the monitor in a stowed position and a use position. The mobile orthodontic treatment system further includes a lift assembly provided on one of a side and an end of the housing to enable disabled people to enter and exit the housing. The lift assembly includes a hydraulic lift configured to move between a stowed position and a use position.

Embodiments of the mobile orthodontic treatment system may include fabricating the bracket is fabricated from steel and includes two lateral members and two cross members secured to the lateral members. One of the two lateral members may be configured to be angled to mate with an interior surface of the housing. The wall mount articulating bracket may include a base that is mounted on the wall of the housing and a movable arm that is secured to the monitor. The digital scanner and the monitor may be secured in the stowed position by an elastic cord that is secured to two cleats mounted on the wall. The digital scanner and the monitor may be secured in the use position by an elastic cord that is secured to the arm of the wall mount articulating bracket and a cleat mounted on a wall of the housing. The lift assembly may be provided at a back end of the housing and mounted on the chassis. The lift assembly may be enclosed by a lift gate provided at the back end of the housing. The housing may include a door providing access into and out of the housing. The mobile orthodontic treatment system further may include a sterilizing machine to sterilize dental equipment, with the sterilizing machine being supported by a cabinet provided within the housing. The mobile orthodontic treatment system further may include a water system to provide water to the sterilization machine. The mobile orthodontic treatment system further may include one or more cooling/heating units mounted on a roof of the housing.

Another aspect of the disclosure is directed to a method of treating a patient requiring orthodontic services at a remote location. In one embodiment, the method comprises: providing a mobile orthodontic treatment system including a mobile trailer, a panoramic machine provided within the mobile trailer, the panoramic machine being configured to obtain a 2-D image of a patient's mouth, a digital scanner and a monitor provided within the housing, the digital scanner being configured to obtain a 3-D image of the patient's mouth and display the image on the monitor, and a lift assembly to enable disabled people to enter and exit the mobile trailer; moving the trailer to a patient's location; and treating the patient in the mobile orthodontic treatment system by defining a problem based on at least one 2-D image and at least one 3-D image of the patient's mouth, designing a treatment strategy based on the problem, and providing a treatment strategy for the patient.

Embodiments of the method further may include applying an apparatus to the patient's teeth to move the patient's teeth. Applying the apparatus may include scheduling periodic visits of the patient by moving the trailer to a location convenient to the patient. Additional 2-D and 3-D images of the patient's mouth may be taken. The apparatus may be altered based on the additional 2-D and 3-D images of the patient's mouth. The method further may include treating multiple patients at a location where the trailer is moved. The method further may include storing records of the patient within the trailer. The method further may include dental equipment within the trailer.

DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures:

FIGS. 13-15 are perspective views of a water system deployed within the mobile orthodontic treatment facility.

DETAILED DESCRIPTION OF THE DISCLOSURE

It is to be appreciated that embodiments of the systems and apparatuses discussed herein are not limited in application to the details of construction and the arrangement of components set forth in the following description or illustrated in the accompanying drawings. The systems and apparatuses are capable of implementation in other embodiments and of being practiced or of being carried out in various ways. Examples of specific implementations are provided herein for illustrative purposes only and are not intended to be limiting. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Embodiments of the present disclosure are directed to a mobile orthodontic treatment system that includes a travel trailer specifically configured to perform orthodontic treatment services. In a certain embodiment, the trailer is pulled by a vehicle, such as a pickup truck. In another embodiment, a recreational vehicle can be used to house the orthodontic treatment equipment. The trailer can embody any length or width sufficient to support orthodontic treatment equipment and to enable personnel within the trailer to perform orthodontic services. In one embodiment, the trailer includes a lift assembly to enable disabled patients in wheel chairs, for example, to enter and leave the trailer.

The trailer is configured with a panoramic machine to enable orthodontic service providers to obtain 2-D dental X-ray examination to capture the entire mouth in a single image. The panoramic machine is uniquely secured to the trailer within an interior of the trailer to ensure that it is safely secured when transporting the trailer. The trailer further includes a digital scanner that is also uniquely secured to the trailer. Other types of dental equipment can be provided, such as sterilization equipment. The trailer is fitted with utilities (power, water, cooling/heating, etc.) to enable orthodontic service providers to provide a full range of orthodontic services.

Figure 1:
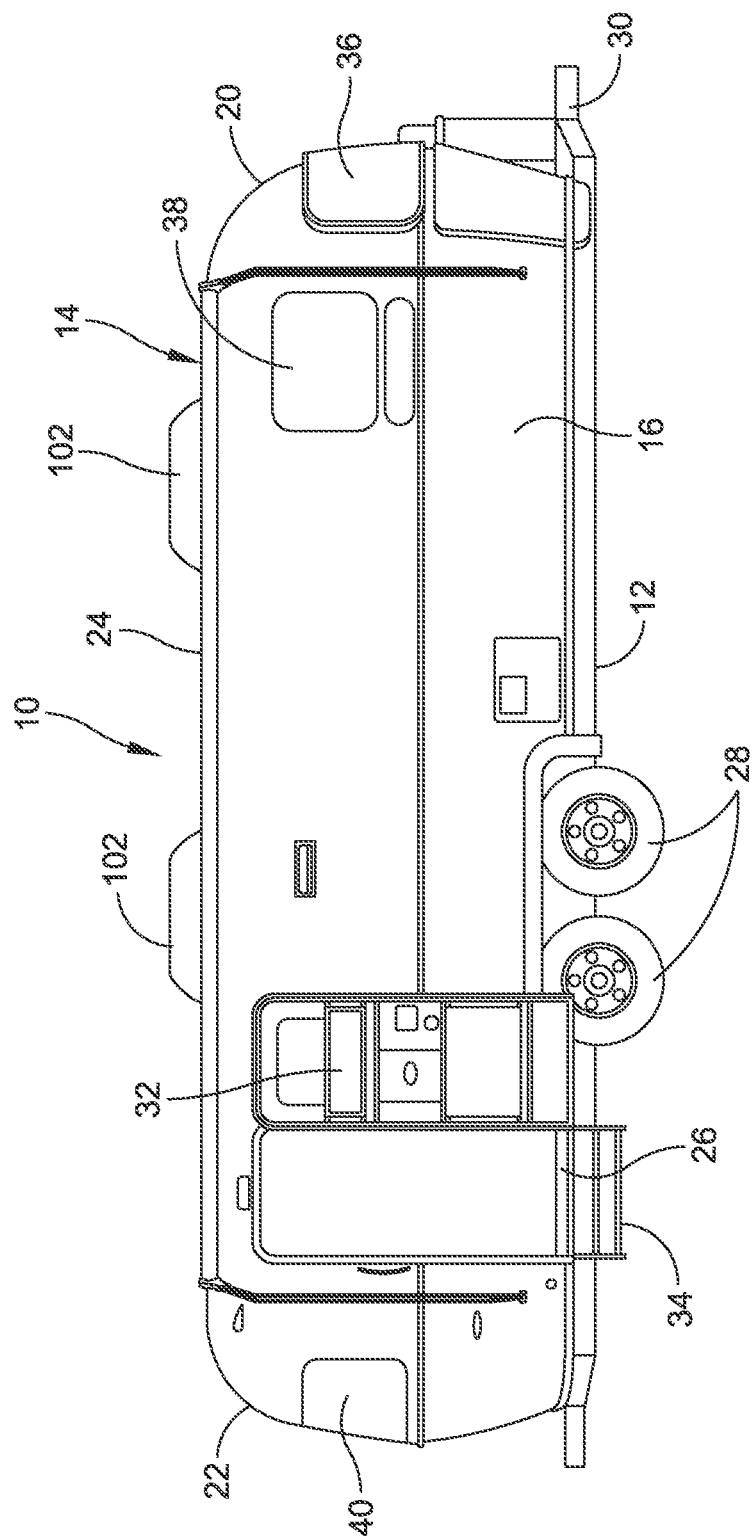
FIG. 1 is a side elevational view of a mobile orthodontic treatment facility of an embodiment of the present disclosure.
Figure 2:
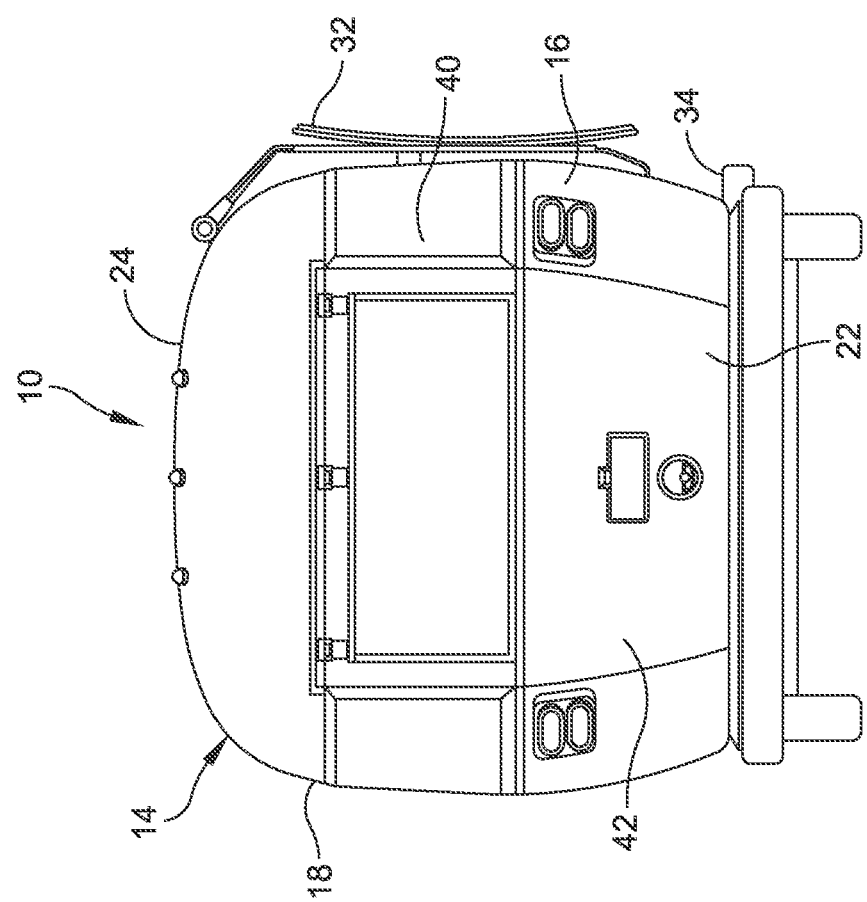
FIG. 2 is an end elevational view of the mobile orthodontic treatment facility.

Referring to the drawings, and more particularly to FIGS. 1 and 2, a mobile orthodontic treatment facility is generally indicated at 12. As shown, the mobile orthodontic treatment facility 12 embodies a trailer that is capable of being transported over roadways to treat patients requiring orthodontic services. Thus, any reference to the trailer shall refer to the mobile orthodontic treatment facility 10.

As shown in FIG. 1, the trailer 10 is configured to allow for the easy transportation of the trailer preferably by a truck, such as a pick-up truck, over roadways. In the shown embodiment, the trailer 10 includes a chassis 12 and a generally rectangular housing generally indicated at 14 that is supported by the chassis. The housing 14 includes two long sides 16, 18, two opposite ends 20, 22, a roof 24 and a floor 26. The chassis 12 includes a wheel assembly that can include two or four wheels, each wheel indicated at 28. In the shown embodiment, four wheels 28 are provided. Provided at the front of the chassis 12 is a trailer mount 30 that enables the trailer 10 to be releasably secured to a trailer hitch provided on the vehicle.

The size and shape of the trailer 10 can be selected based on where the trailer will be traveling. For example, a smaller trailer can be employed when traveling narrow streets and/or congested areas. Thus, the size and shape of the trailer 10 may vary between embodiments, and it is preferable that the size and shape of the trailer are configured to allow the passage of the trailer on roadways and under bridges. Moreover, as mentioned above, the trailer 10 can form part of a recreational vehicle thus obviating the need for a truck to pull the trailer. A compartment of the recreational vehicle can be configured to support the orthodontic treatment equipment and personnel.

The trailer 10 may also include one or more doorways for entering and leaving. For example, in the shown embodiment, the side 16 of the housing 14 of the trailer 10 includes a door 32 that serves as a main entrance to an interior of the trailer. The door 32 is secured to the side 16 of the trailer by a hinge to enable the door to swing between a closed position and an open position. A ramp or stairs 34 may be provided to enable service personnel and patients to enter and exit the trailer 10.

The trailer 10 further includes several windows to enable natural light to enter the interior of the trailer. As shown, the trailer 10 includes windows 36, 38, 40 provided in the front end 20, the side 16 and the back end 22 of the trailer, respectively. The other side 18 can include one or more window as well. Also, skylights can be provided in the roof 24 of the housing 14 of the trailer 10.

Figure 3:
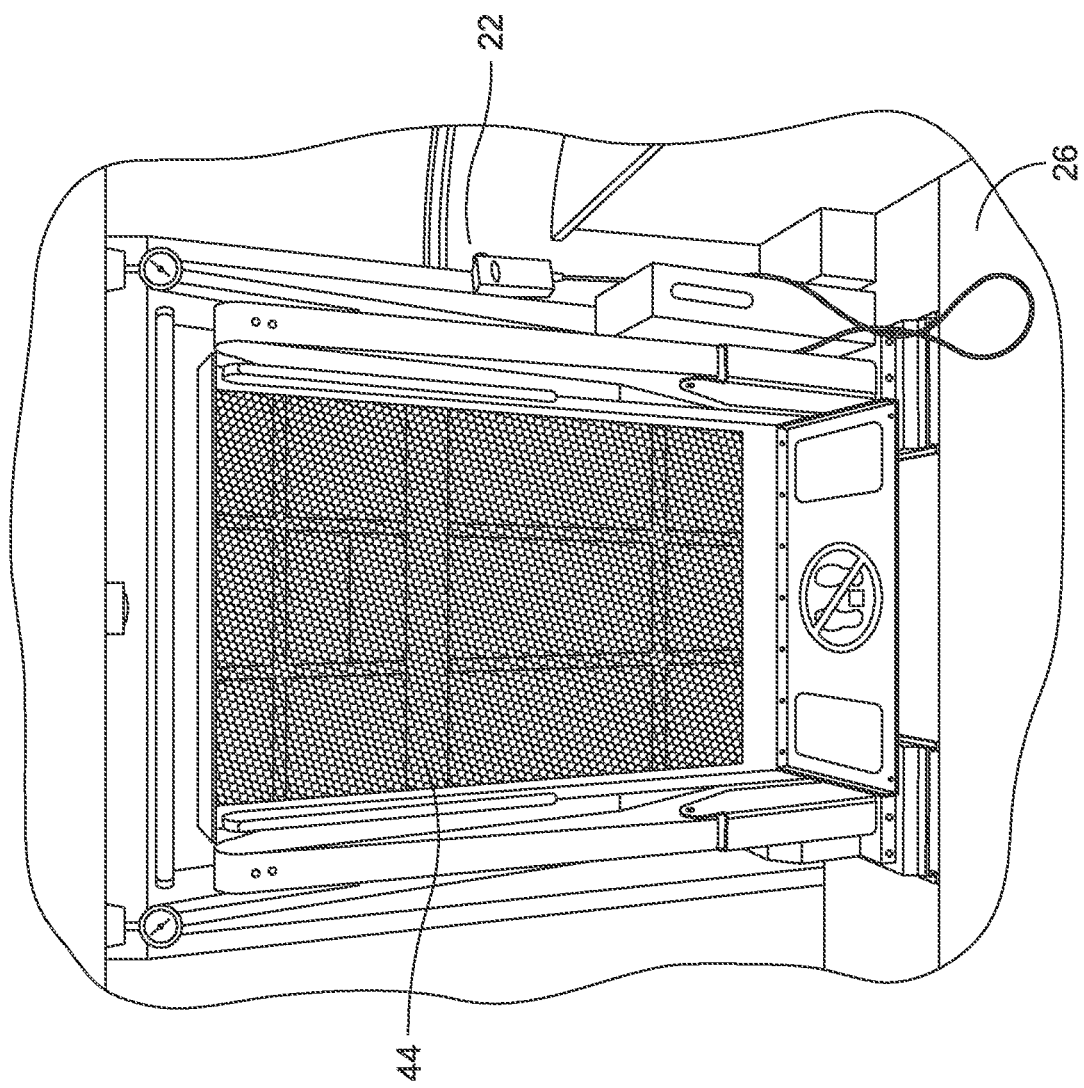
FIG. 3 is a perspective view of a lift assembly of the mobile orthodontic treatment facility in a closed or collapsed position.
Figure 4:
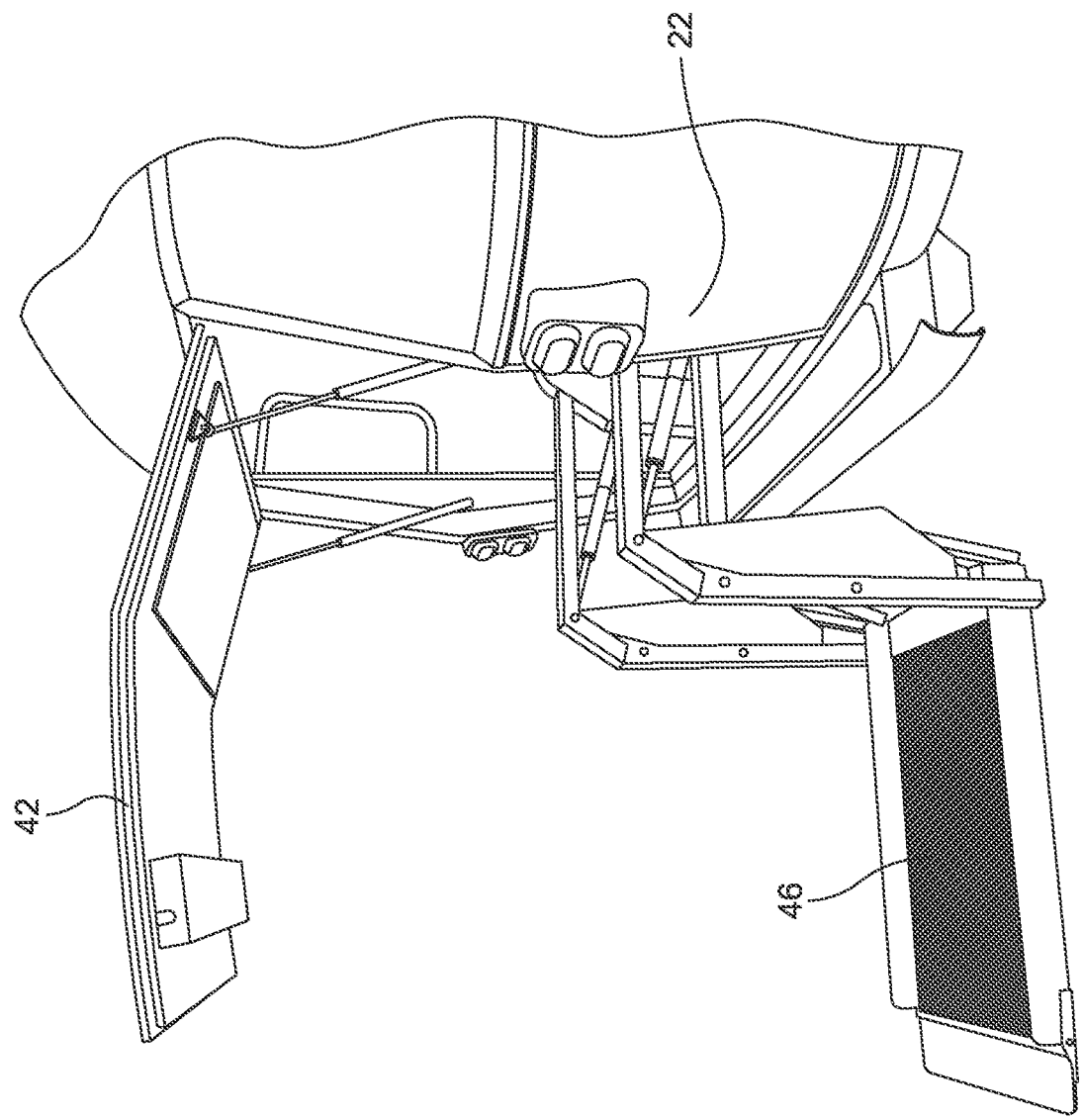
FIG. 4 is a perspective view of the lift assembly in an extended or use position.

Referring to FIGS. 3 and 4, the back end 22 of the housing 14 of the trailer 10 may define an entry that serves as a secondary entrance. In one embodiment, the back end 22 of the housing 14 of the trailer 10 includes a lift gate 42 that can be opened and closed. When the lift gate 42 is opened, a lift assembly 44 is revealed to assist people with entering and exiting the interior of the trailer 10. In one embodiment, the lift assembly 44 includes a hydraulic lift mounted on the back end 22 of the housing 14 of the trailer 10 on the chassis 12. The lift assembly 44 is configured to facilitate the movement of people and/or equipment in and out of the interior of the trailer 10. FIG. 3 illustrates the lift assembly 44 in a closed or stowed position. FIG. 4 illustrates the lift assembly 44 in a deployed or use position. When deployed, the lift assembly 44 is configured to move the patient from outside the trailer 10 to inside the interior of the trailer. Once used, the lift assembly 44 can be manipulated to move back to its closed position with the lift gate 42 closed to enclose the back end 22 of the housing 14 of the trailer 10. In one embodiment, the lift assembly is a Ricon® S-Series® ADA transit use wheelchair and standee lift. Additional doors may be provided depending on the size of the trailer 10. These additional doors may also use ramps or stairs to enable personnel to enter and/or exit the trailer 10.

Although not shown, the trailer 10 may also include one or more hydraulic legs for leveling and/or stabilizing the trailer and thus the floor. In one embodiment, the trailer 10 has four hydraulic legs located proximate to each corner of the trailer. Each leg is configured to extend down from the undersurface and engages the ground. A level can be provided to ensure the floor of the trailer is level.

Figure 5:
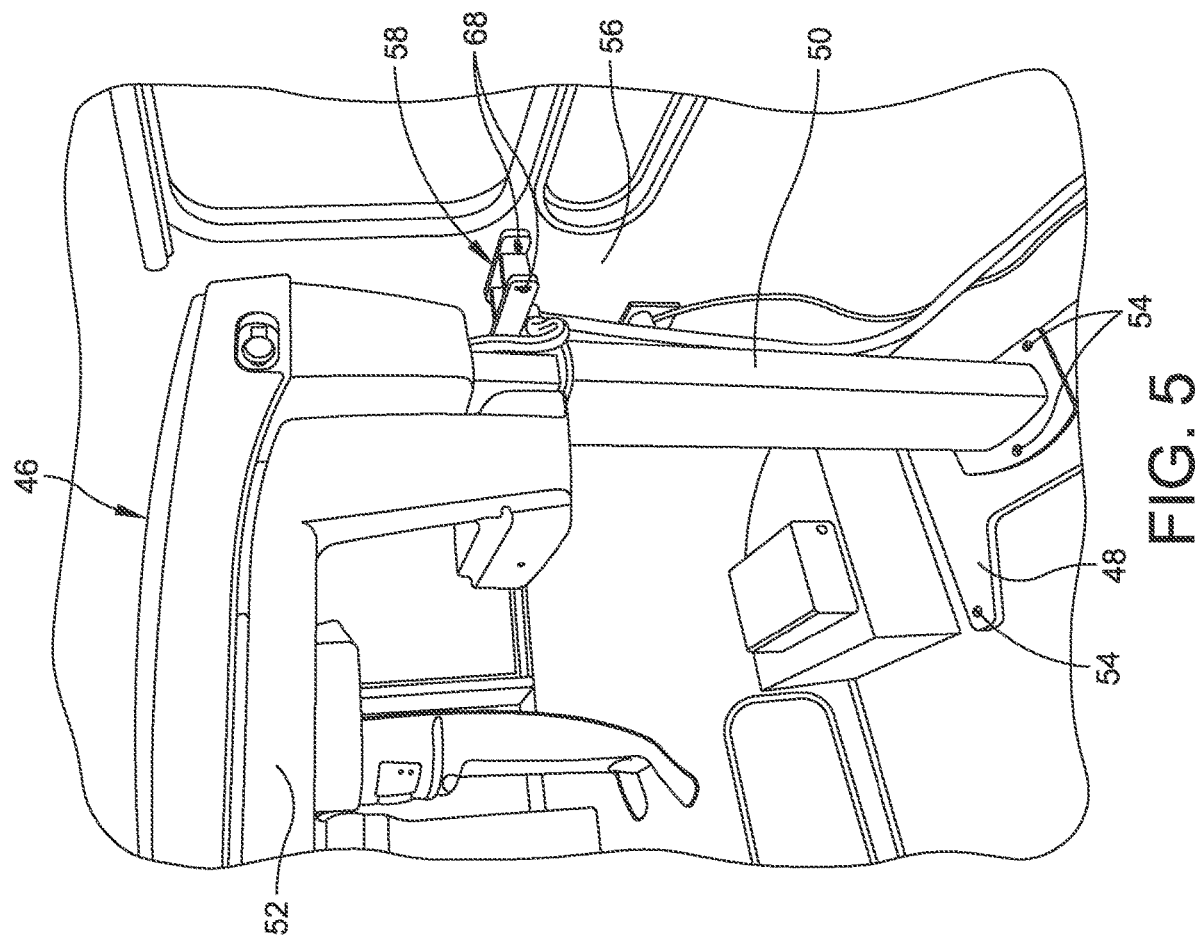
FIG. 5 is a perspective view of a panoramic machine deployed within the mobile orthodontic treatment facility.
Figure 6:
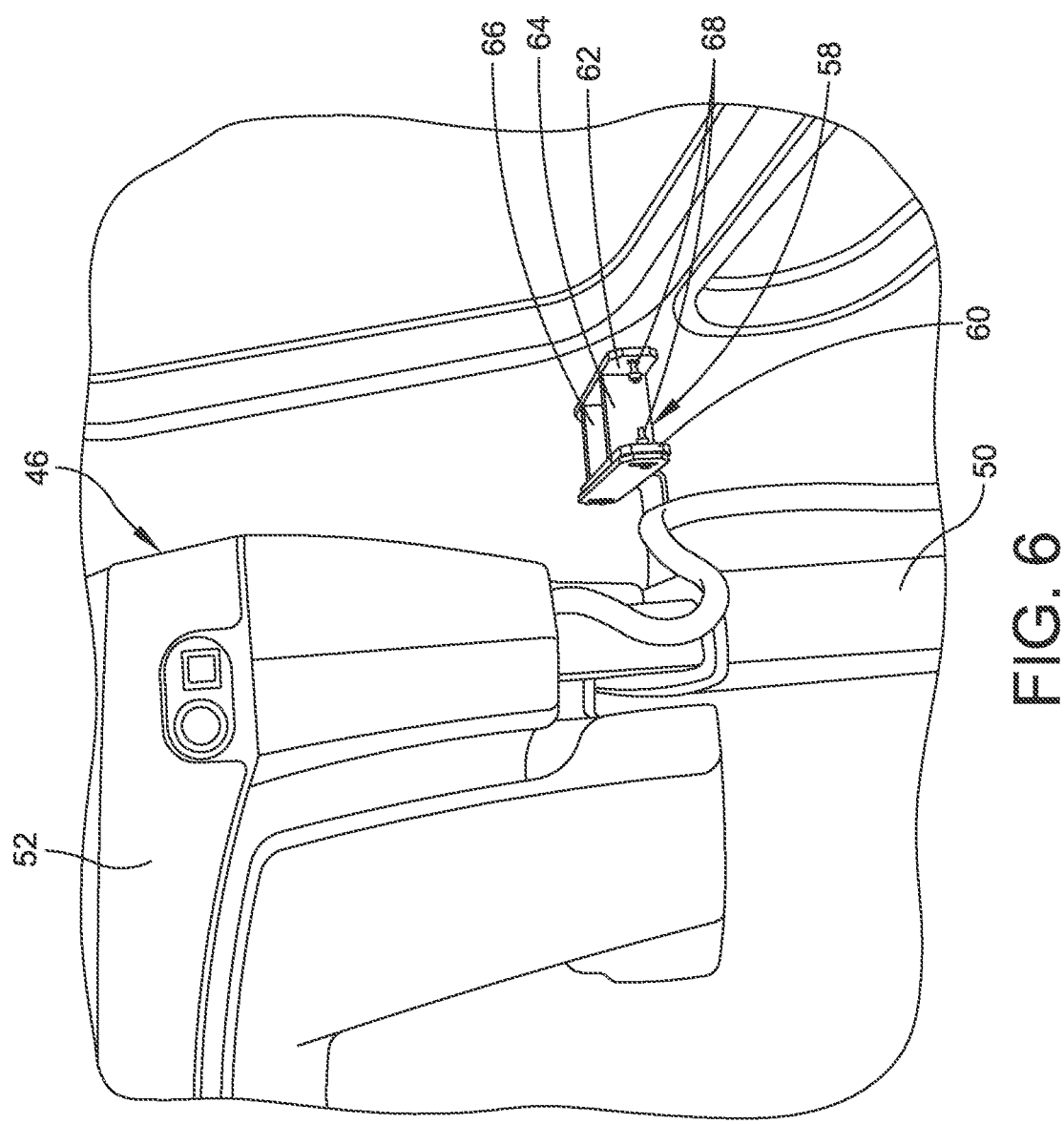
FIG. 6 is another perspective view of the panoramic machine secured to an inner wall of the mobile orthodontic treatment facility by a bracket.

Referring to FIGS. 5 and 6, a panoramic machine, generally indicated at 46, is housed within the interior of the trailer 10. In one embodiment, the panoramic machine 46 includes a base 48, an upright stanchion 50 extending upwardly from the base, and an image detector 52 that includes a horizontal rotating arm configured to hold an X-ray source and a moving film mechanism. In one embodiment, the panoramic machine is a Carestream Dental® CS8100 panoramic imaging system. The base 48 of the panoramic machine 46 is bolted to the floor of the housing 14 of the trailer 10 by bolts, each indicated at 54. Additionally, to provide lateral stability, the upright stanchion 50 of the panoramic machine 46 is secured to a wall 56 of the trailer 10 by a specialized bracket, generally indicated at 58, designed to secure the panoramic machine in place. As best shown in FIG. 6, the bracket 58 is fabricated from ¼- or ⅜-inch steel and includes two lateral members 60, 62 and two cross members 64, 66 secured as by welding to the lateral members. As shown, lateral member 62 can be configured to be angled to mate with the wall 56 of the trailer 10 if the wall is slightly off angle. The bracket 58 is fixedly secured to the panoramic machine and to the side of the trailer by bolts, each indicated at 68, that extend through openings formed in flanges of the lateral members 60, 62. The arrangement is such that the panoramic machine 46 is fixedly secured to the trailer 10 to withstand normal movements of the trailer when traveling along a roadway.

Figure 7:
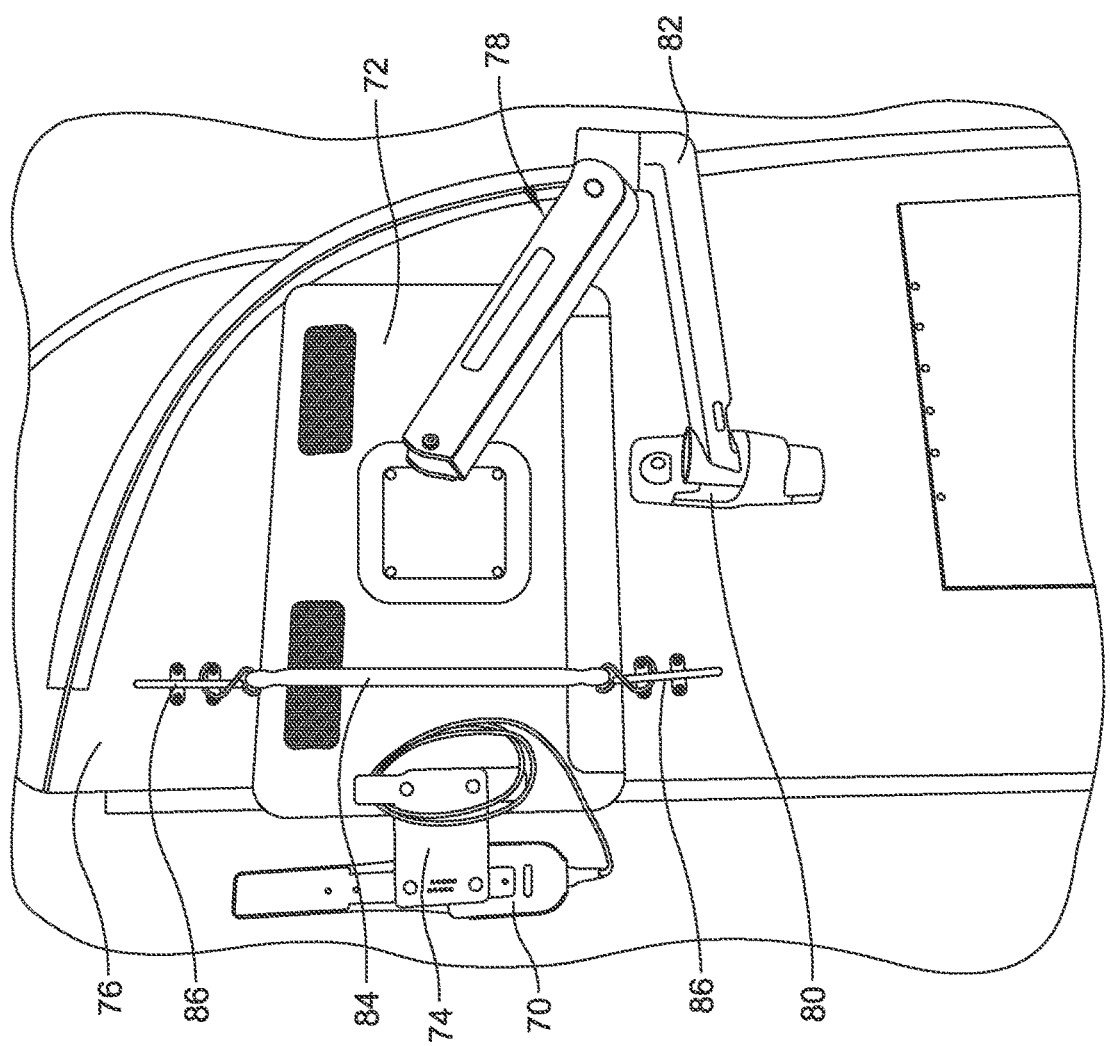
FIG. 7 is a perspective view of a digital scanner deployed within the mobile orthodontic treatment facility in a secured position.
Figure 8:
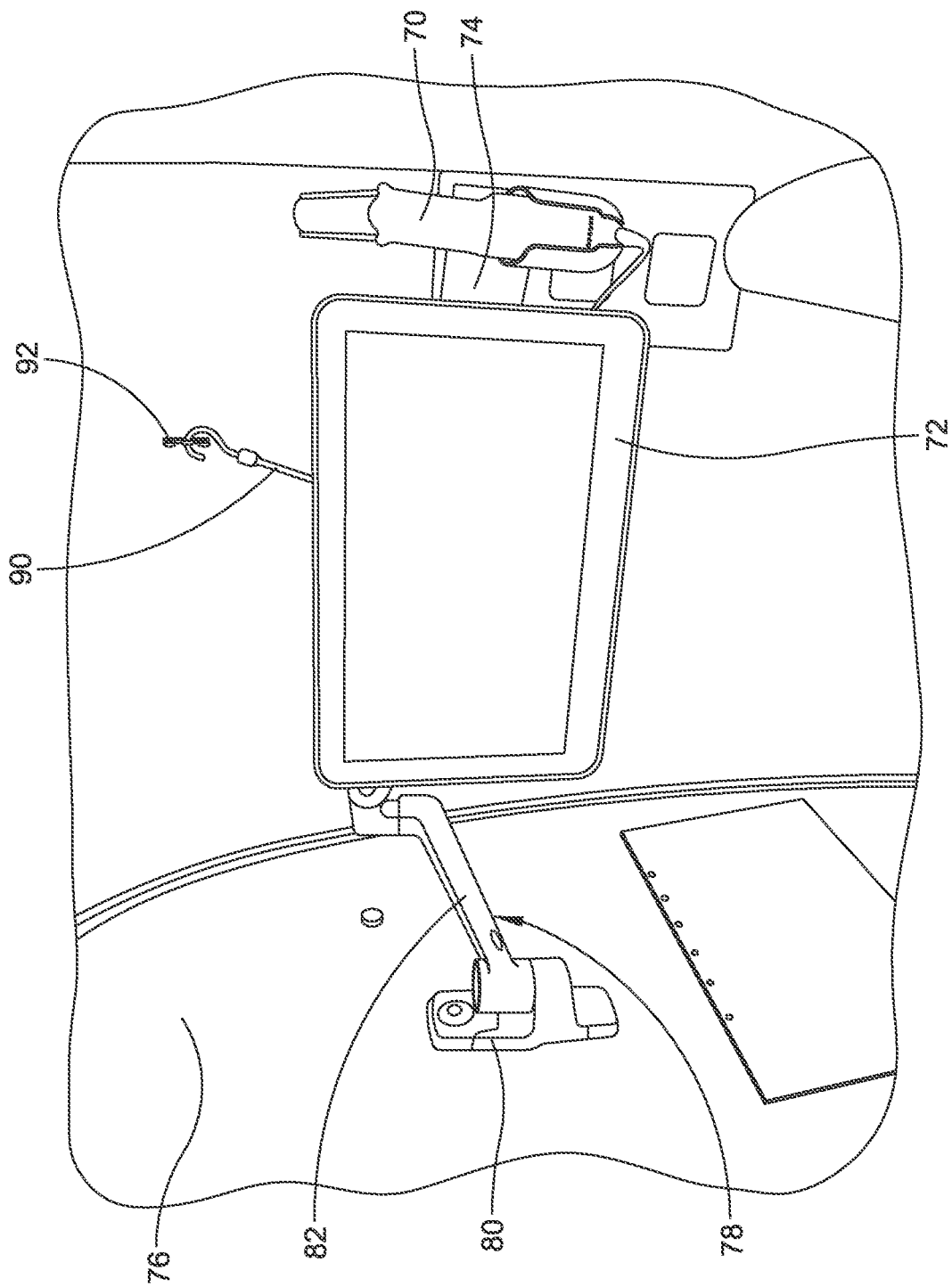
FIG. 8 is a perspective view of the digital scanner in a use position.

Referring to FIGS. 7 and 8, a digital scanner 70 and a monitor 72 is housed within the interior of the trailer 10. In one embodiment, the digital scanner 70 is configured to obtain a 3-D image of the patient's mouth and display the image on the monitor 72. In one embodiment, the digital scanner 70 is secured to the monitor by a bracket 74. In one embodiment, the digital scanner is an iTero Element® 2 scanner. The digital scanner 70 and the monitor 72 are mounted on an interior wall 76 of the housing 14 of the trailer 10 by a wall mount articulating bracket, generally indicated at 78. As shown the articulating bracket 78 includes a base 80 that is mounted on the interior wall 76 and a movable arm 82 that is secured to the monitor 72. FIG. 7 illustrates the digital scanner 70 and the monitor 72 in a stowed position by an elastic cord 84 that is secured to two cleats, each indicated at 86, mounted on the interior wall 76. The elastic cord 84 secures the face of the monitor 72 against the interior wall 76 to protect the monitor and the digital scanner 70 when transporting the trailer 10. FIG. 8 illustrates the digital scanner 70 and the monitor 72 in an extended or use position in which the monitor 72 is secured to a wall 88 of the interior of the trailer 10 by another elastic cord 90 that is secured to the arm 82 and a cleat 92 mounted on the wall.

Figure 9:
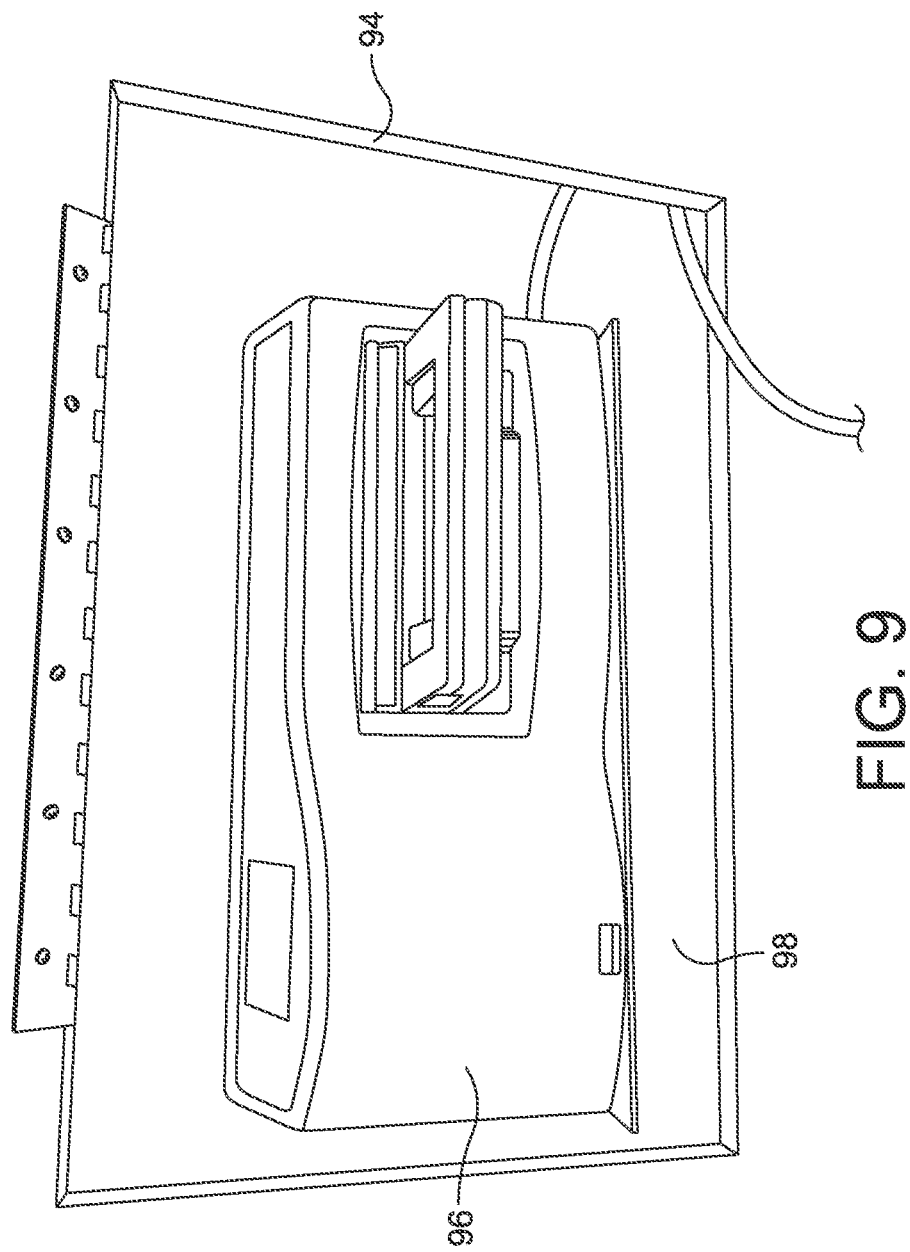
FIG. 9 is a perspective end view of a sterilizing machine deployed within the mobile orthodontic treatment facility.
Figure 10:
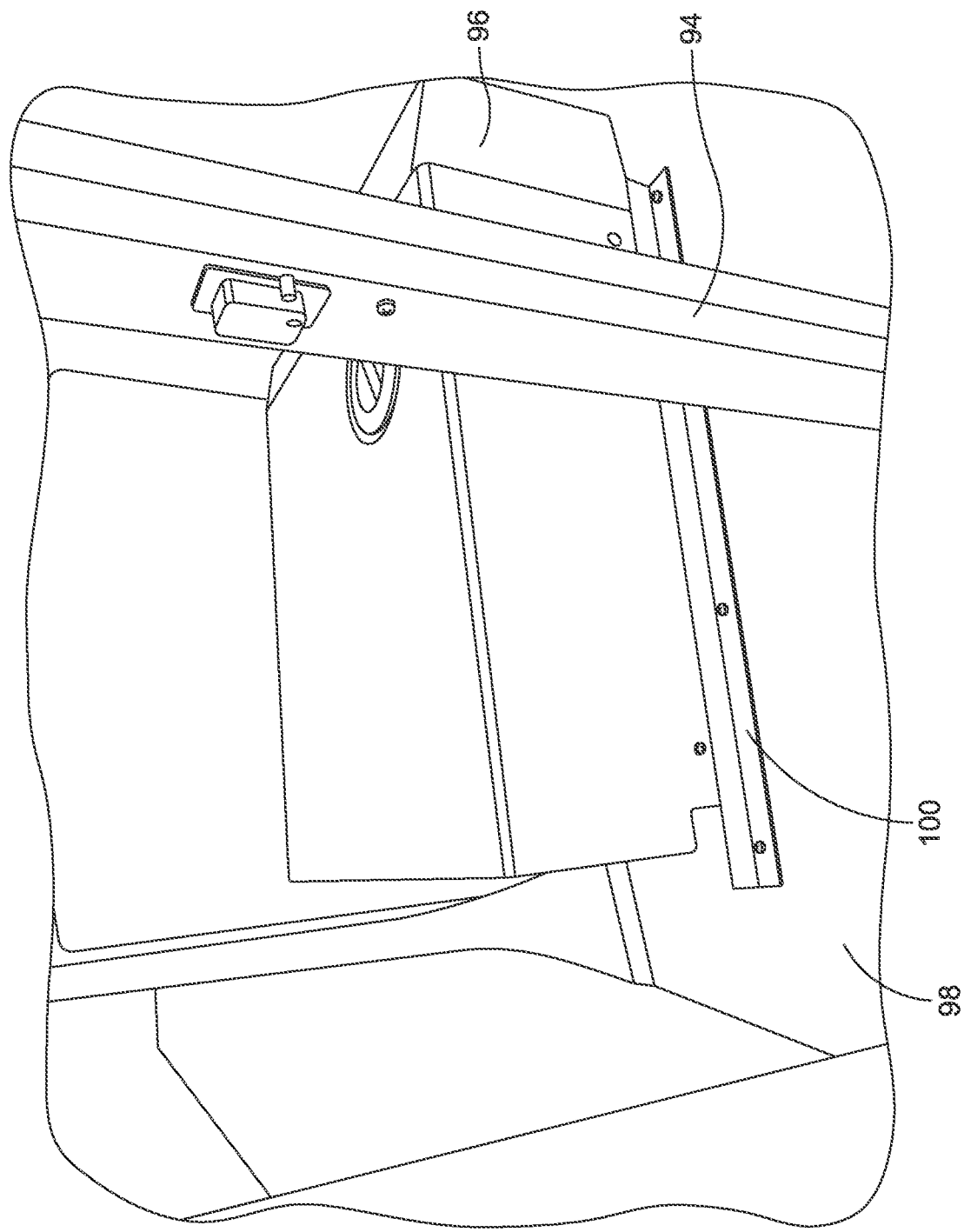
FIG. 10 is a perspective side view of the sterilizing machine.

Referring to FIGS. 9 and 10, a portion of a cabinet 94 is shown to house a sterilizing machine 96 to sterilize dental equipment. In one embodiment, the sterilizing machine 96 is a SciCan STATIM 5000 G4 cassette autoclave offered by SciCan Inc. of Canonsburg, Pa. The autoclave is configured to use only a small, specific amount of water required for each cleaning cycle. Water is introduced into a heating device, referred to as a "steam generator," rapidly heated and converted to steam in seconds. The autoclave further includes a high-resolution color touchscreen to display messages, current cycle information and customizable icons. In one embodiment, the sterilizing machine 96 is mounted on a shelf 98 within the cabinet by brackets 100 in the form of angle iron.

Figure 11:
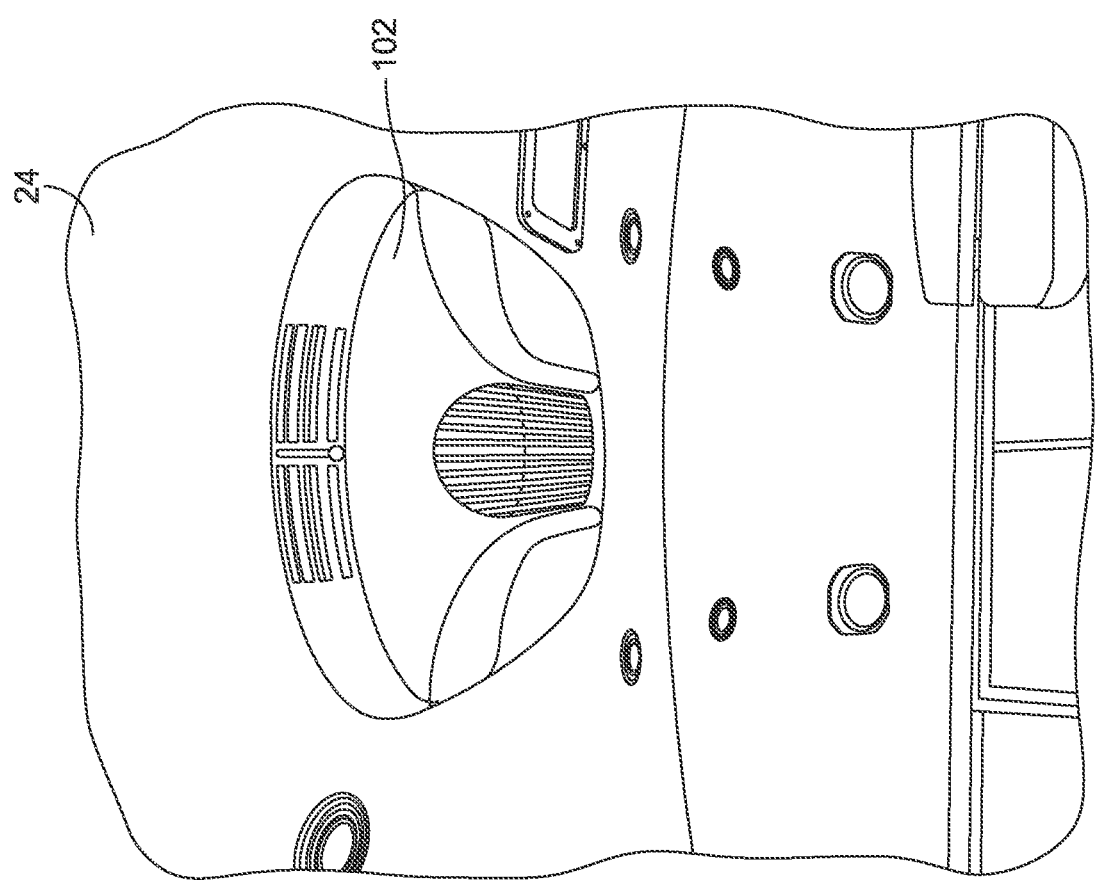
FIG. 11 is perspective view of a cooling/heating unit deployed within the mobile orthodontic treatment facility.

Referring additionally to FIG. 11, the trailer 10 further includes one or more cooling/heating units mounted on the trailer. As shown in FIG. 1, the trailer 10 includes two cooling/heating units, each indicated at 102, which are mounted on the roof 24 of the trailer to provide cooling and/or heating within the interior of the trailer. Any number of cooling/heating units can be provided depending on the size of the trailer 10. Moreover, any type of cooling/heating units can be provided. For example, units secured to the sides or ends of the trailer may be provided.

Figure 12:
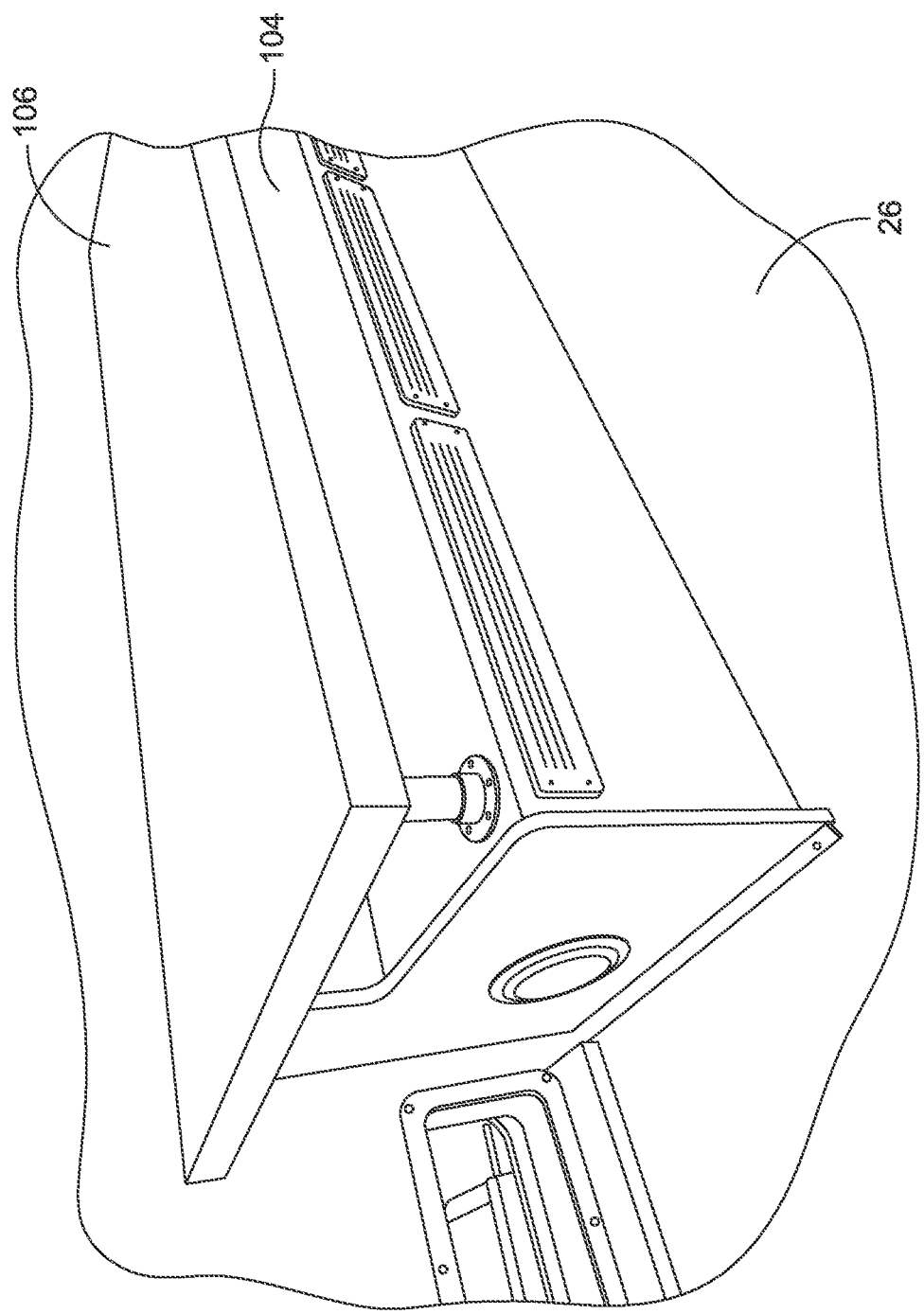
FIG. 12 is a perspective view of a table deployed within the mobile orthodontic treatment facility.

Referring to FIG. 12, one or more tables or benches, such as bench 104 and table 106, can be provided to provide suitable workspace within the trailer 10. The trailer 10 can be configured with any number of tables and benches depending on the size of the trailer.

Figure 13:
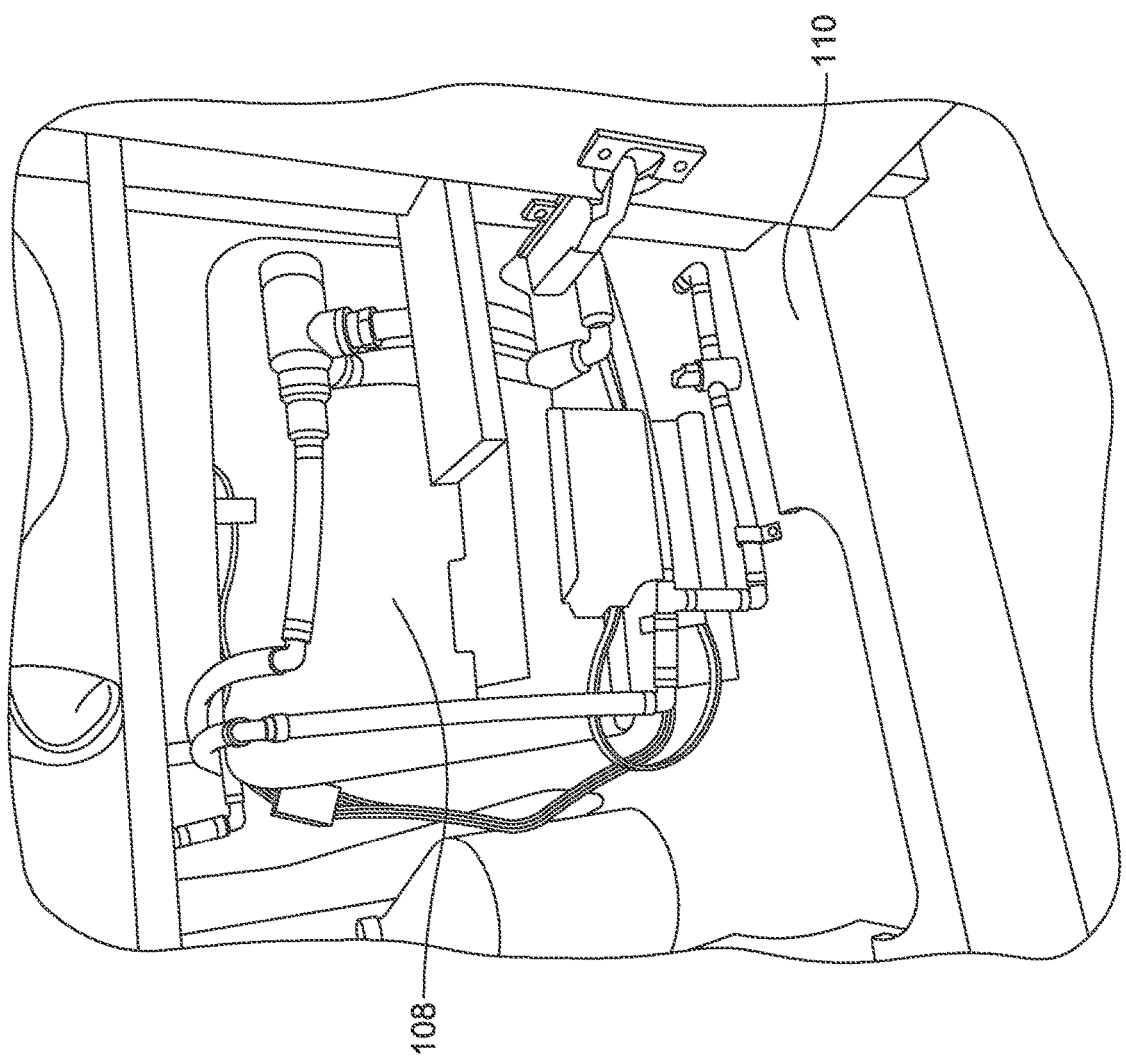
Figure 14:
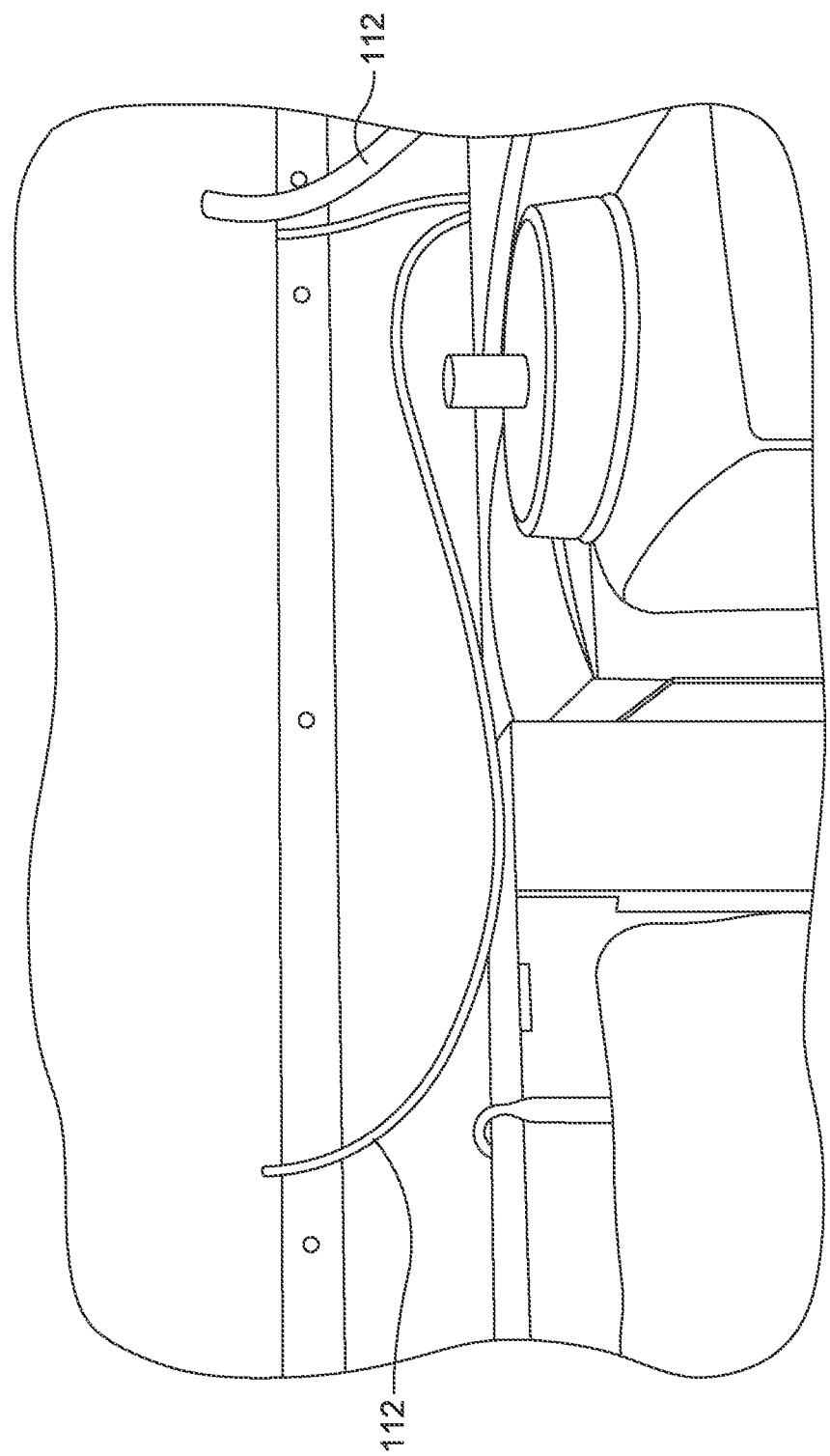

Referring to FIGS. 13-15, the trailer 10 includes a water system to provide clean and filtered potable water. In one embodiment, the water system provides water to the sterilization machine 96. FIG. 13 illustrates a water pump unit 108 positioned within a cabinet 110 and configured to provide water to the sterilization machine 96 and a sink mounted on a cabinet within the housing 14. FIG. 14 illustrates hoses 112 configured to drain water from the sink, for example, or from the sterilizing machine 96. FIG. 15 illustrates a holding tank 114 configured to store and hold waste water from the hoses 112. As shown, the holding tank 114 is mounted on the chassis 12.

The trailer may also include power generation, biohazard waste disposal, lighting, and air filtration for the treatment areas. Supplies may be stored in overhead cabinets and/or fixed cabinets. Dental personnel workstations are located to maximize viewing and monitoring of all patients and provide work areas for examination and other related duties. Telephone and data connections can be provided within the trailer. Computers are connected via a server mounted onboard the trailer.

The trailer may further include a communication system for providing high-speed communication for the orthodontic treatment facility. The communication system may have, among other things, a satellite dish mounted on the trailer, for example, the roof of the trailer, a receiver/processor, and one or more additional monitors positioned within the trailer. The communication system provides a real-time video and audio communication link between the mobile orthodontic treatment facility and a home office, for example.

The mobile orthodontic treatment facility is configured to include utilities, including oxygen and required piping, as well as related equipment and instruments. Additional hardware including cabinets for storage is also provided. The mobile orthodontic treatment facility may also include supply carts capable of being secured for storing and moving around supplies.

The trailer can further include a dental chair, which is sometimes referred to as a dental engine. The dental chair is a large chair-side appliance that is typically used in a dental office. The dental chair includes a source of mechanical and/or pneumatic power to one or more handpieces used by the orthodontist. The dental chair can also be configured to include a small faucet and a spit-sink to rinse the patient's mouth. Suction hoses and a water nozzle can be provided to clean the patient's mouth. Other devices supported by the dental chair can include an ultrasonic cleaning appliance, a small table to hold an instrument tray, a work light, and a computer monitor or display.

As mentioned, the trailer is configured to be pulled by a vehicle, such as a pickup truck having a trailer hitch. However, the chassis of the trailer can be configured to be pulled by any type of trailer configuration. Moreover, as mentioned above, the trailer can be embodied in a recreational vehicle.

A method of treating a patient requiring orthodontic services is also disclosed herein. For a new patient, the orthodontist would typically recognize the various characteristics of a malocclusion or dentofacial deformity, define the problem, design a treatment strategy based on the problem, and provide a treatment strategy. Depending on the problem or problems, it is possible that there may be more than one course of treatment for the patient. A typical treatment plan can include removing teeth for overcrowded mouths and applying an apparatus for moving the patient's teeth. When using an apparatus, such as braces (visible or invisible), a treatment plan can take one to two years to complete, with the apparatus being altered, albeit slightly, every four to six weeks. Thus, a patient over the course of a two-year period can expect to visit the orthodontist up to fifteen visits.

One advantage associated with trailer 10 is that the trailer can be moved to a place convenient to the patient. For example, the trailer can be brought to the patient's work or school location. The trailer can thus services many patients located in a common location. In one embodiment, a patient enters the trailer through the main door or through the primary or main entrance or through the secondary entrance if disabled. The patient's records can be stored in the one or more cabinets provided in the trailer or stored electronically on the computer. For a new patient, as described above, to evaluate the patient, the orthodontist would most likely obtain a panoramic X-ray and a digital scan of the patient's teeth. Thus, the patient would obtain the panoramic X-ray at the panoramic machine and a scan at the digital scanner. The digital scanner would have to be extended to us deployed or use position. The patient's mouth can be examined in the dental chair.

For a return patient, an updated panoramic X-ray and an updated digital scan of the patent can be obtained by the panoramic machine and the digital scanner, respectively. Based on the results, the orthodontist can alter the apparatus to progress the patient's treatment. This process continues until the patient's treatment is completed.

The mobile orthodontic treatment facility of embodiments of the present disclosure has several advantages. The mobile orthodontic treatment facility is easily transported over the roadways without requiring any extensive transportation means. The mobile orthodontic treatment facility is capable of being completely self-sufficient and may include generator power, running portable water, biohazardous waste disposal, lighting, heating, air conditioning and air filtration.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method of treating a patient requiring orthodontic services at a remote location, the method comprising:
    providing a mobile orthodontic treatment system including
        a mobile trailer including a chassis and a housing supported by the chassis, the housing having two sides, two opposite ends, a roof, and a floor, the chassis having a wheel assembly,
        a panoramic machine provided within the housing of the mobile trailer, the panoramic machine being configured to obtain a 2-D image of a patient's mouth, the panoramic machine including a base, an upright stanchion extending upwardly from the base, and an image detector, the base of the panoramic machine being secured to the floor of the housing of the mobile trailer, the upright stanchion being secured to a side or an end of the housing by a bracket,
        a digital scanner and a monitor provided within the housing of the mobile trailer, the digital scanner being configured to obtain a 3-D image of the patient's mouth and display the image on the monitor, the digital scanner and the monitor being mounted on a wall of the housing by a wall mount articulating bracket configured to support the digital scanner and the monitor in a stowed position and a use position, and
        a lift assembly provided on one of a side and an end of the housing to enable disabled people to enter and exit the housing of the mobile trailer, the lift assembly including a hydraulic lift configured to move between a stowed position and a use position;
    moving the mobile trailer to a patient's location; and
    treating the patient in the mobile orthodontic treatment system by defining a problem based on at least one of a 2-D image and a 3-D image of the patient's mouth, designing a treatment strategy based on the problem, and providing a treatment strategy for the patient.

2. The method of claim 1, further comprising applying an apparatus to the patient's teeth to move the patient's teeth.

3. The method of claim 2, wherein applying the apparatus includes scheduling periodic visits of the patient by moving the mobile trailer to a location convenient to the patient.

4. The method of claim 3, wherein additional 2-D and/or 3-D images of the patient's mouth are taken.

5. The method of claim 4, wherein the apparatus is altered based on the additional 2-D and/or 3-D images of the patient's mouth.

6. The method of claim 1, further comprising treating multiple patients at a location where the mobile trailer is moved.

7. The method of claim 1, further comprising storing records of the patient within the mobile trailer.

8. The method of claim 1, further comprising sterilizing dental equipment within the mobile trailer.

9. A mobile orthodontic treatment system comprising:
a mobile trailer;
at least one of a panoramic machine and a digital scanner provided within the mobile trailer, the panoramic machine being configured to obtain a 2-D image of a patient's mouth, the digital scanner being configured to obtain a 3-D image of the patient's mouth; and
a lift assembly provided on one of a side and an end of the mobile trailer to enable disabled people to enter and exit the mobile trailer, the lift assembly including a hydraulic lift configured to move between a stowed position and a use position,
wherein the panoramic machine includes a base, an upright stanchion extending upwardly from the base, and an image detector, the base of the panoramic machine being secured to a floor of the mobile trailer, the upright stanchion being secured to a side or an end of the mobile trailer by a bracket, the bracket being fabricated from steel and includes two lateral members and two cross members secured to the lateral members, one of the two lateral members being configured to be angled to mate with an interior surface of the mobile trailer.

10. The mobile orthodontic treatment system of claim 9, wherein the lift assembly is provided at a back end of the mobile trailer.

11. The mobile orthodontic treatment system of claim 10, wherein the lift assembly is enclosed by a lift gate provided at the back end of the mobile trailer.

12. The mobile orthodontic treatment system of claim 9, wherein the mobile trailer includes a door providing access into and out of the mobile trailer.

13. The mobile orthodontic treatment system of claim 9, further comprising a sterilizing machine to sterilize dental equipment, the sterilizing machine being supported by a cabinet provided within the mobile trailer.

14. The mobile orthodontic treatment system of claim 9, wherein the digital scanner is mounted on a wall of the mobile trailer by a wall mount articulating bracket configured to support the digital scanner and the monitor in a stowed position and a use position.

15. The mobile orthodontic treatment system of claim 14, wherein the wall mount articulating bracket includes a base that is mounted on the wall of the mobile trailer and a movable arm that is secured to the monitor.

16. The mobile orthodontic treatment system of claim 15, wherein the digital scanner is secured in the stowed position by an elastic cord that is secured to at least one cleat mounted on the wall.

17. The mobile orthodontic treatment system of claim 15, wherein the digital scanner is secured in the use position by an elastic cord that is secured to the arm of the wall mount articulating bracket and a cleat mounted on the wall of the mobile trailer.

* * * * *